(12) United States Patent
Hanai et al.

(10) Patent No.: US 8,021,886 B1
(45) Date of Patent: Sep. 20, 2011

(54) METHOD FOR DETERMINING WHETHER OR NOT A MAMMAL IS AFFECTED WITH A LUNG CANCER

(75) Inventors: Yosuke Hanai, Osaka (JP); Hiroaki Oka, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 12/959,052

(22) Filed: Dec. 2, 2010

Related U.S. Application Data

(60) Provisional application No. 61/302,818, filed on Feb. 9, 2010.

(51) Int. Cl.
*G01N 33/48* (2006.01)
(52) U.S. Cl. ............ 436/64; 436/63; 436/127; 436/128; 436/161
(58) Field of Classification Search .................... 436/63, 436/64, 127, 128, 161, 173
See application file for complete search history.

(56) References Cited

U.S. PATENT DOCUMENTS

| 2006/0160237 | A1* | 7/2006 | Du | 436/129 |
| 2010/0126254 | A1* | 5/2010 | Du | 73/61.52 |

OTHER PUBLICATIONS

Matsumura et al. Plos One, vol. 5, issue 1, Jan. 2009, e8819, pp. 1-11.*

* cited by examiner

*Primary Examiner* — Maureen Wallenhorst
(74) *Attorney, Agent, or Firm* — McDermott Will & Emery LLP

(57) ABSTRACT

The present disclosure relates to a method for assessing if a patient is affected with a lung cancer. The method includes analyzing the presence and amount of cyclohexanone contained in the urine excreted from the patient and determining if the presence and amount of cyclohexanone is indicative of lung cancer.

6 Claims, 8 Drawing Sheets

METHOD FOR DETERMINING WHETHER OR NOT A MAMMAL IS AFFECTED WITH A LUNG CANCER

CROSS-REFERENCE TO RELATED APPLICATION

This application claims priority to provisional application Ser. No. 61/302,818, filed Feb. 9, 2010, the contents of which are incorporated by reference herein.

BACKGROUND OF THE INVENTION

1. Field of the Invention

The present disclosure relates to a method for determining whether or not a patient is affected with a lung cancer. Patients which are to be the subjects of the method of the present disclosure are preferably mammals including humans.

2. Description of the Related Art

Substances that are present in large amounts in cancer cells but are either not present, or only present in small amounts in normal cells are known. Such substances are referred to as "tumor markers". Tumor marker tests, in general, quantitatively determine a tumor marker in blood, and have been used for the purpose of aiding diagnosis of cancer, or confirming the degree of progression of cancer. As such, in order to determine the presence of a tumor marker in a patient, it is typical that a sample of blood is drawn from the patient.

Conventional tumor markers are high molecular substances such as hormones, enzymes, isozymes, or fragmented proteins. Since there are great differences among individuals in blood levels of these conventional tumor markers, usability in diagnosing cancer has been unsatisfactory due to the occurrence of false negatives and false positives.

SUMMARY OF THE INVENTION

The present Applicants investigated utilization of a volatile low molecular compound, which has otherwise has not been investigated as a tumor marker, and consequently discovered that by quantitatively determining cyclohexanone contained in the urine excreted from a mammal, determination is enabled as to whether or not the mammal is affected with a lung cancer. Accordingly, the present disclosure was accomplished.

An aspect of the present disclosure relates to a method for determining whether or not a patient is affected with a lung cancer, the method comprising the steps of:

obtaining a urine sample from the patient;

measuring the concentration of cyclohexanone contained in the urine sample; and determining that the patient is suffering from lung cancer if the concentration is equal to or greater than 1 µM.

The patients preferably a primate or a human

According to the present disclosure, a method of determination is provided which is useful for diagnosing lung cancer in mammals.

The above objects, other objects, features and advantages of the present disclosure will be apparent from the following detailed description of preferred embodiments with reference to attached drawings.

DETAILED DESCRIPTION OF PREFERRED EMBODIMENTS

Figure 1:
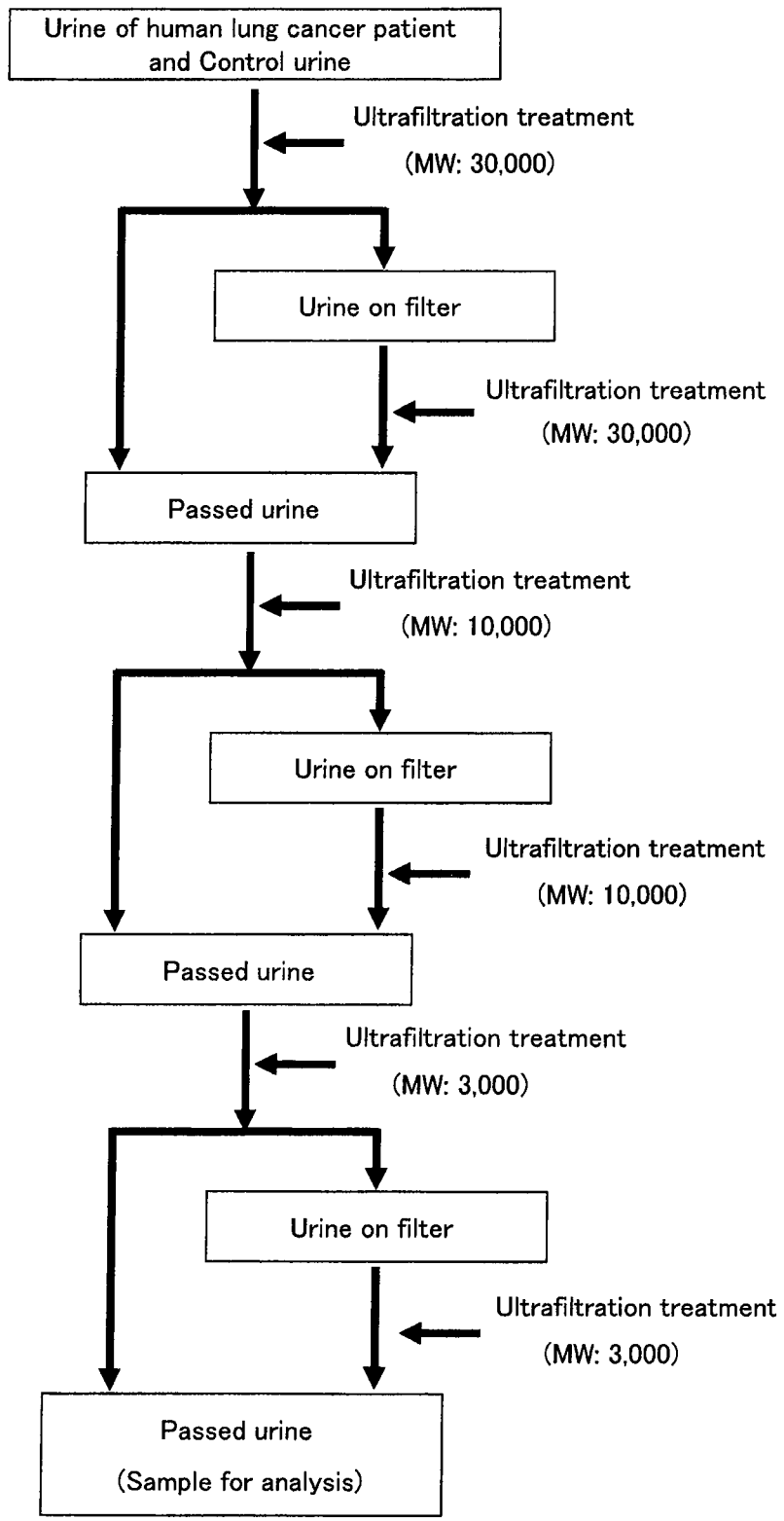
FIG. 1 shows a scheme for illustrating a procedure of ultrafiltration of a urine sample.

In a general aspect of the disclosure, urine from a patient is collected and the concentration of the cyclohexanone contained in the urine excreted from the patient is measured. Based on the concentration of the cyclohexanone measured, it determined that the patient is suffering from lung cancer if the concentration is equal to or greater than 1 µm.

A feature of the above general aspect of the invention may be that the concentration of the cyclohexanone is measured using gas chromatography, liquid chromatography or any other known method or combination of methods of measuring organic compounds.

Another feature of the above general aspect of the disclosure may be that the lung cancer is selected from the group consisting of squamous cell, adenocarcinoma, non-small cell lung carcinoma (NSCLC), large cell carcinoma and adenosquamous carcinoma.

1. Collection of Urine, and Ultrafiltration of Urine (1) Collecting Method of Urine Urine of a human lung cancer patient was collected from 19 lung cancer patients (Table 1a) corresponding to stages 1A to 3B who participated as volunteers. Control urine was collected from 19 human non-lung cancer patients who were from 36 to 86 years old (Table 1b), and participated as volunteers. Each 1 mL of the urine collected from each patient was dispensed into a 1.5 mL tube, and stored at −80° C. until subjecting to an ultrafiltration treatment.

Table 1a shows age, sex (represented by "Gender"), race, tissue type, stage, and smoking history (represented by "Tobacco History") of the human lung cancer patients. Table 1b shows age, sex, race, diagnosis, and smoking history of the human non-lung cancer patients. Blank columns in the smoking history mean that the subject had no history of smoking. The abbreviation of "COPD" in Table 1b means "Chronic Obstructive Pulmonary Disease".

TABLE 1a

| Subject No. | Age | Gender | Race | Histology | Overall Stage | Tobacco History |
|---|---|---|---|---|---|---|
| 1 | 81 | F | White | Squamous Cell | 1A | Current |
| 2 | 84 | F | White | Adenocarcinoma | 1A | |
| 3 | 81 | F | White | NSCLC-NOS | 1A | Former |

TABLE 1a-continued

| Subject No. | Age | Gender | Race | Histology | Overall Stage | Tobacco History |
|---|---|---|---|---|---|---|
| 4 | 69 | M | White | Squamous Cell | 1A | Current |
| 5 | 65 | F | White | Adenocarcinoma | 1A | Former |
| 6 | 68 | M | White | Adenocarcinoma | 1B | Former |
| 7 | 73 | F | White | Adenosquamous | 1B | Former |
| 8 | 69 | M | White | Squamous Cell | 1B | Former |
| 9 | 71 | M | White | Squamous Cell | 2A | Former |
| 10 | 54 | M | White | Squamous Cell | 2B | Former |
| 11 | 53 | M | White | Large Cell | 2B | Former |
| 12 | 69 | F | White | Adenocarcinoma | 3A | Former |
| 13 | 64 | F | Asian | Adenocarcinoma | 3A | |
| 14 | 64 | M | White | Adenocarcinoma | 3A | Former |
| 15 | 76 | F | White | Adenocarcinoma | 3A | Current |
| 16 | 62 | M | White | NSCLC-NOS | 3B | Former |
| 17 | 81 | M | White | Adenocarcinoma | 3B | Former |
| 18 | 62 | M | White | Squamous Cell | 3B | Former |
| 19 | 55 | M | White | Adenosquamous | 3B | Former |

Race (White: Caucasian, Asian: Asian)
Gender (M = male, F = female)

TABLE 1b

| Subject No. | Race | Age | Gender | Diagnosis | Tobacco History |
|---|---|---|---|---|---|
| 1 | White | 72 | F | COPD | |
| 2 | White | 83 | M | COPD | |
| 3 | Asian | 49 | M | COPD | |
| 4 | Asian | 62 | M | COPD | |
| 5 | White | 54 | F | Asthma | |
| 6 | White | 48 | F | Healthy | Former |
| 7 | White | 49 | F | Healthy | Former |
| 8 | Asian | 50 | F | Healthy | Current |
| 9 | Asian | 38 | F | Healthy | Current |
| 10 | White | 48 | F | Healthy | Former |
| 11 | White | 38 | F | Healthy | Current |
| 12 | White | 47 | F | Heart disease | Former |
| 13 | White | 51 | F | Thyroid disease | Current |
| 14 | White | 59 | M | Healthy | Current |
| 15 | White | 55 | M | Asthma | Current |
| 16 | Asian | 49 | F | Healthy | Current |
| 17 | White | 61 | M | Heart disease | Current |
| 18 | White | 62 | M | Hypertension | Current |
| 19 | White | 36 | F | Hypertension | Current |

Race: White = Caucasian, Asian = Asian
Gender: M = male, F = female (2) Ultrafiltration of Urine Sample The urine of the human lung cancer patient and the control urine were subjected to ultrafiltration according to the procedure shown in FIG. 1. The urine of the human lung cancer patient and the control urine (each 1 mL) which had been frozen and stored at −80° C. were thawed on ice. After thawing, centrifugal separation (13,000 g×10 min) was carried out to remove insoluble matter. The thus obtained supernatant was set on a Microcon centrifugation system filter unit YM-30 (30-kDa cutoff, Millipore, Bedford, Mass.), and subjected to centrifugal separation (12,000 G, 0° C., 90 min). The urine that passed through the filter was set on a Microcon centrifugation system filter unit YM-10 (10-kDa cutoff, Millipore, Bedford, Mass.), and subjected to centrifugal separation in a similar manner as described above. The urine that passed through the filter was set on a Microcon centrifugation system filter unit YM-3 (3-kDa cutoff, Millipore, Bedford, Mass.), and subjected to centrifugal separation in a similar method as described above.

When the urine remained on the filter after each centrifugal separation, the remaining urine was transferred on a new filter, and similar centrifugal separation was repeated until no urine remained on the filter. The filtrate that passed through the filter unit YM-3 was dispensed into 1.5 mL tube. The filtrate was stored at 4° C. as a urine sample for analysis until it is analyzed with gas chromatography.

Figure 2:
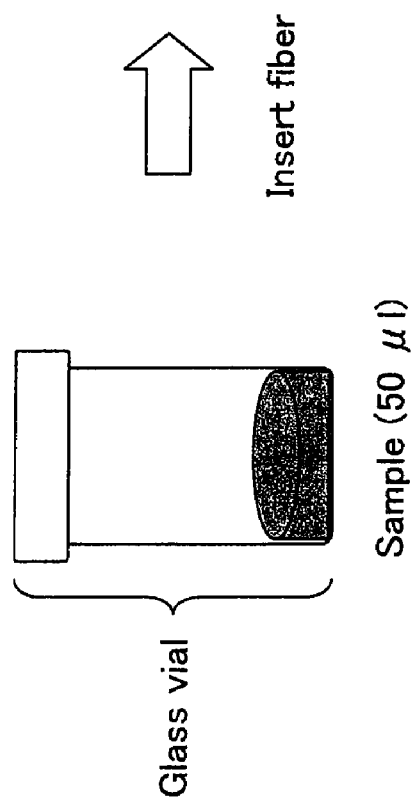
FIG. 2 shows a schematic view for illustrating a trapping method of volatile components contained in a urine sample by a SPME method.
Figure 2:
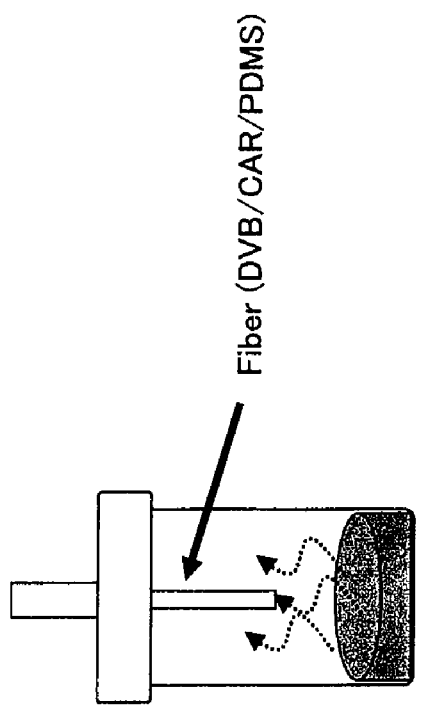

2. Analysis of Volatile Components Using Solid Phase Micro Extraction (SPME) Method (1) Extraction of Volatile Components Volatile components in the urine sample for analysis were extracted by a solid phase micro extraction. Each urine sample for analysis in a volume of 50 µL was placed into a 1.5 mL glass vial, and the vial was sealed airtight using a lid with septum. The vial was set into a heating block, and incubated at 40° C. for 10 min. As shown in FIG. 2, a Stable Flex DVB/CAR/PDMS fiber (SUPELCO, Inc., 2-layer fiber, film thickness: 50 µm/30 µm) was inserted into the vial for 40 min, to extract the volatile components in the head space to the fiber.

Before extracting of the volatile components, the fiber was subjected to a heat treatment at 230° C. for 30 min to eliminate any volatile component from the fiber, and thereafter inserted into the vial.

(2) Method for Analyzing Volatile Components

After extraction, the volatile components were thermally desorbed and analyzed. The analysis was performed using a gas chromatography (GC) or a gas chromatography-mass spectrometry (GC-MS). The extracted fiber was inserted into the injector of each instrument.

As a gas chromatography with a flame ionization detector (FID), GC-4000 (GL Sciences Inc.) was used. Analysis conditions were as shown below.

Column: INERTCAP Pure-WAX; internal diameter: 0.25 mm, length: 30 m, film thickness=0.25 µm Column temperature: 40° C. (5 min)→temperature elevation at a rate of 4° C./min→250° C. (5 min)

Carrier gas: helium 100 kPa

Injection: 230° C., splitless (closed 5 min)

Detector: FID (250° C.)

As the gas chromatography-mass spectrometry apparatus, GCMS-QP2010 (Shimadzu Corporation) was used. Analysis conditions were as shown below.

Column: InertCap® Pure-WAX; internal diameter: 0.25 mm, length: 30 m, film thickness=0.25 µm Column temperature: 40° C. (5 min)→temperature elevation at a rate of 4° C./min→250° C. (5 min)

Carrier gas: helium 100 kPa

Injection: 230° C., splitless (closed 5 min)

Ionization process: Electron Impact method

Figure 3:
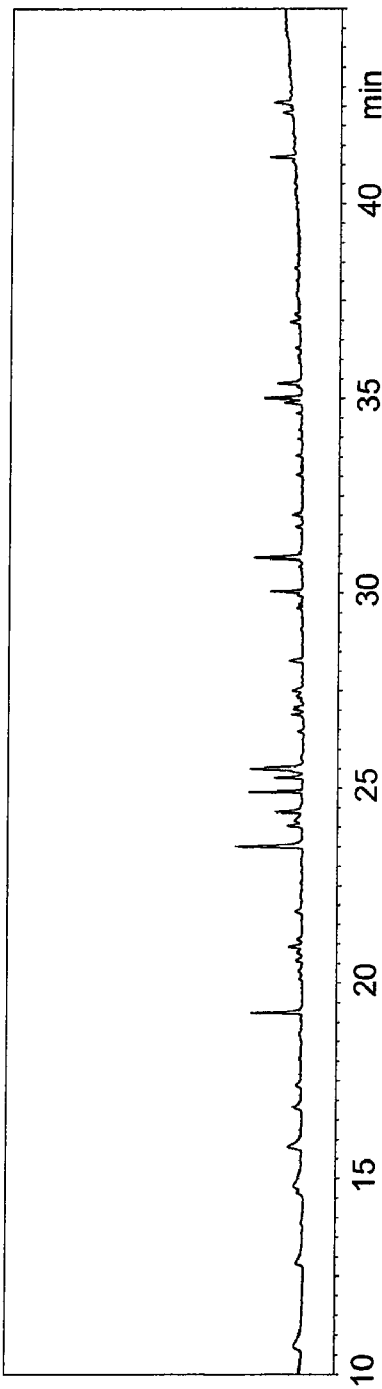
FIG. 3(a) shows a gas chromatogram of a control urine sample.
FIG. 3(b) shows a gas chromatogram of a urine sample from a human lung cancer patient.
Figure 3:
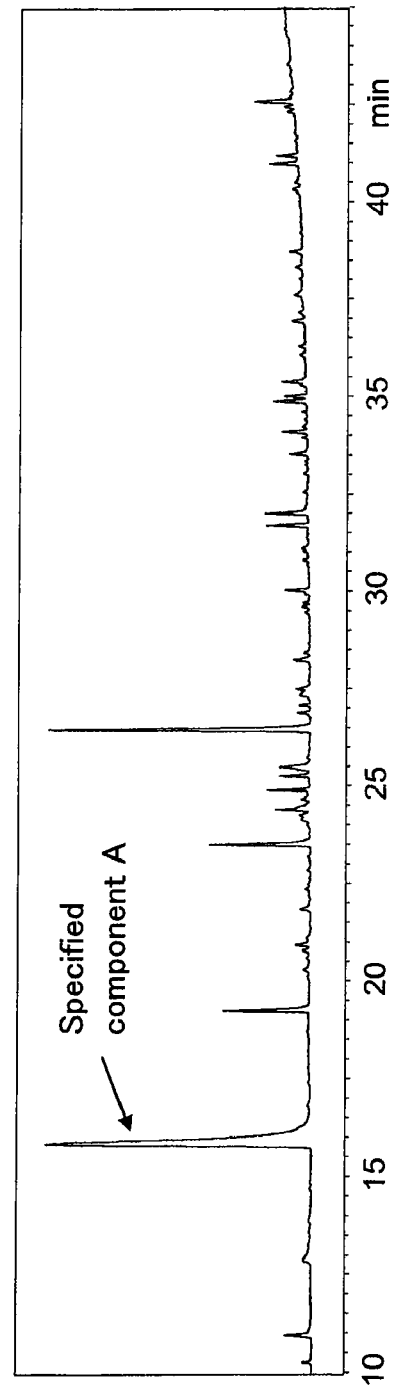

3. Identification and Quantitative Determination of Specified Component that Serves as Marker of Cancer (1) Comparison of Gas Chromatogram A gas chromatogram (FIG. 3*a*) of the control urine (urine of a human non-lung cancer patient) was compared with a gas chromatogram of the lung cancer urine (urine of a human lung cancer patient) (FIG. 3*b*). An increased peak present in the urine of the human lung cancer patient was identified by visual inspection. Hereinafter, the peak is referred to as "specified component A".

Figure 4:
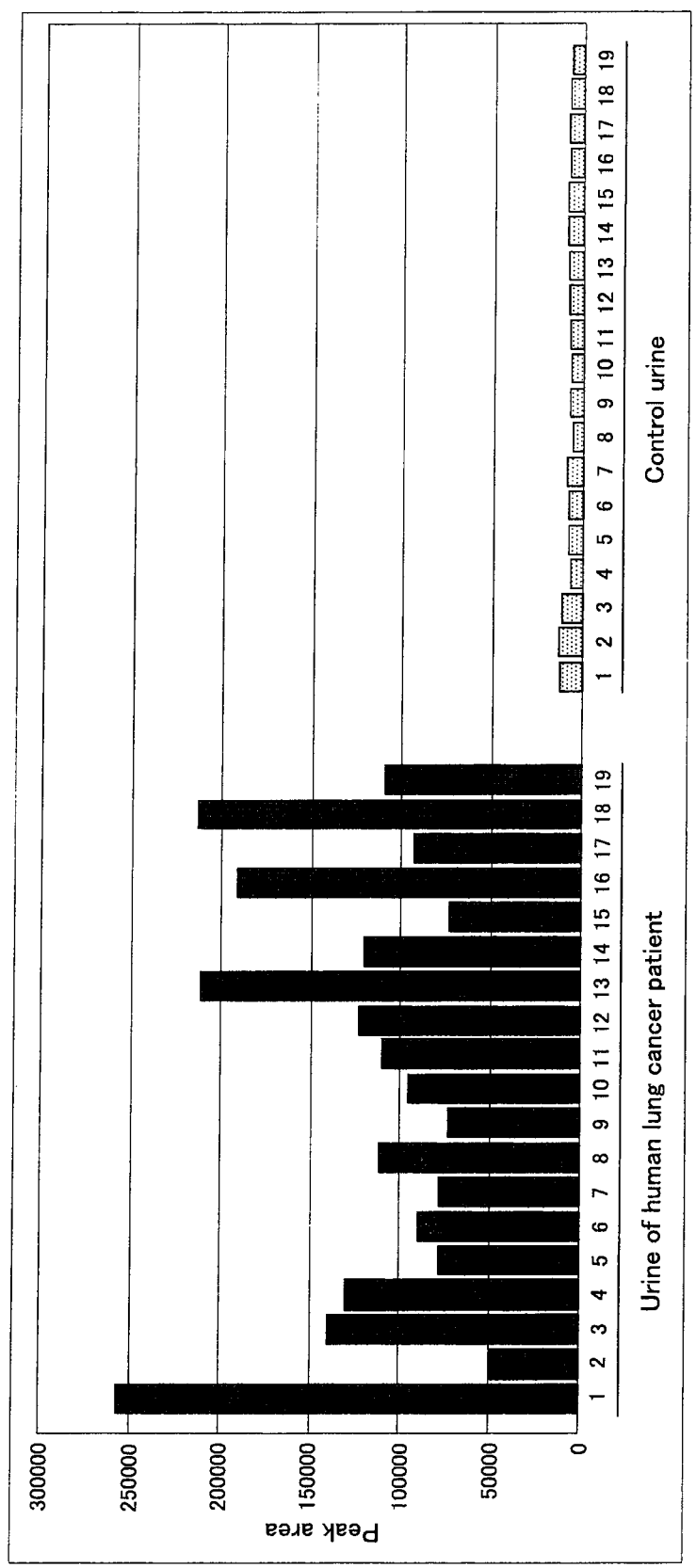
FIG. 4 shows graphs demonstrating the peak area of a specified component A in gas chromatograms.

The peak areas of the specified component A in all samples of the lung cancer urine and the control urine were calculated from each gas chromatogram. FIG. 4 shows the peak areas of the specified component A. Numerical values presented along the horizontal axis of FIG. 4 show the patient number listed in Table 1a and Table 1b. As is seen from FIG. 4, the peaks of the specified component A for the urine of the human lung cancer patient had significantly greater area than the peaks of the specified component A for the control urine.

Figure 5:
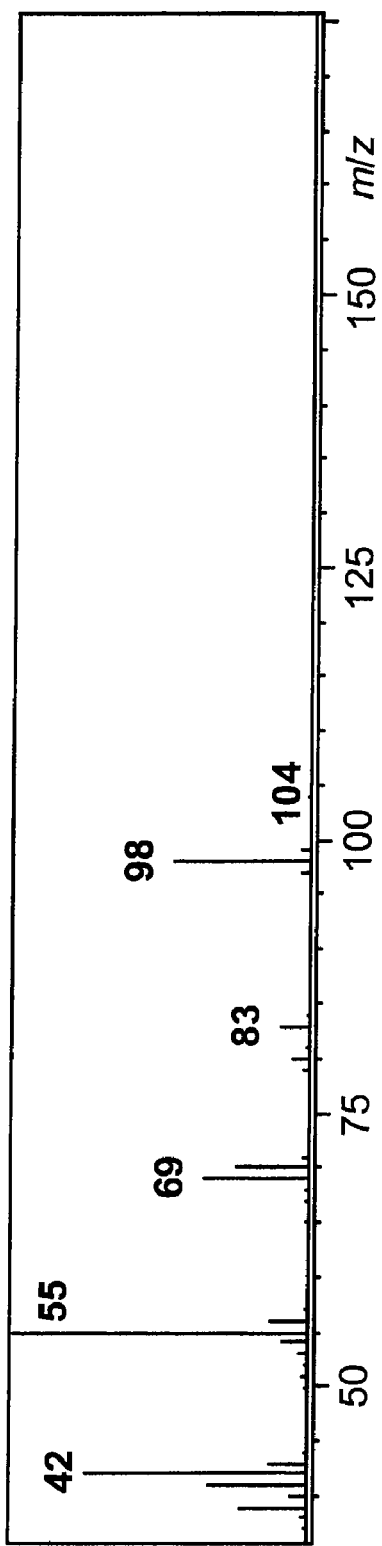
FIG. 5(a) shows a MS spectrum of the specified component A.
FIG. 5(b) shows a MS spectrum of cyclohexanone listed in NIST database.
Figure 5:
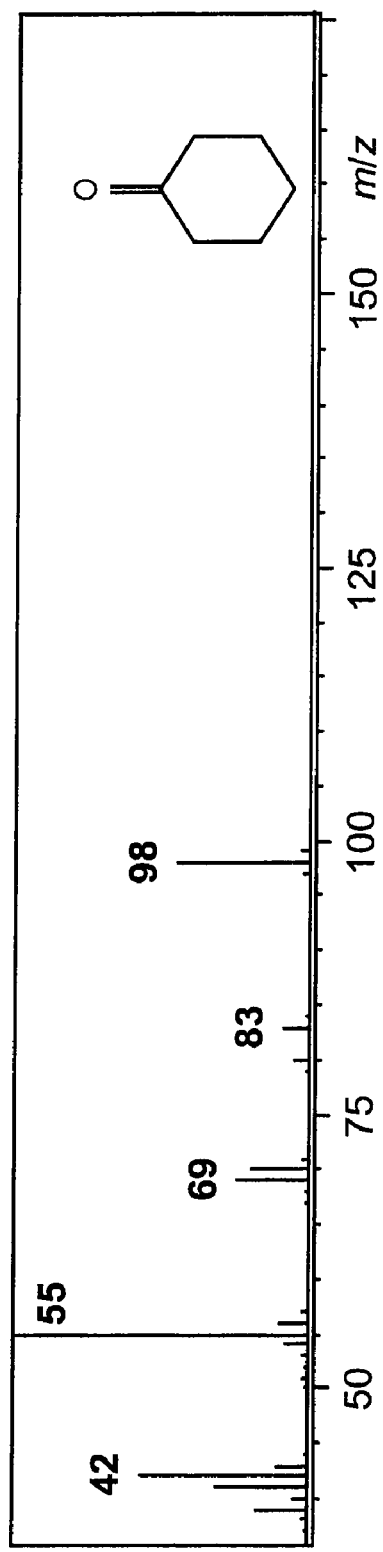

(2) Searching of Candidate Compound FIG. 5*a* shows an MS spectrum of the specified component A. Based on the m/z value on the MS spectrum of the specified component A observed, a candidate compound of the specified component A was searched using NIST database (NIST147.LIB) attached to the gas chromatography-mass spectrometry. As a result, cyclohexanone corresponded to the information from the NIST database with a similarity of 98 (perfect match=100). FIG. 5b shows the MS spectrum of cyclohexanone listed in the NIST database.

(3) Identification of Specified Component A

Figure 6:
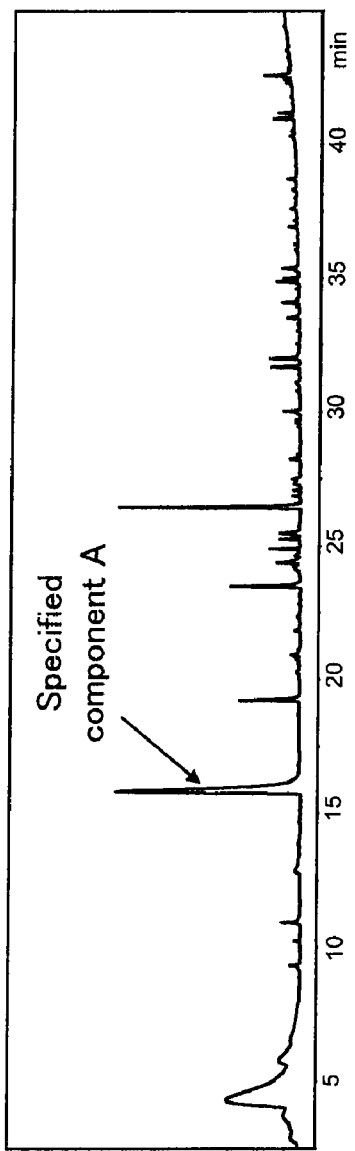
FIG. 6(a) shows a GC chromatogram of a urine sample from a human lung cancer patient.
FIG. 6(b) shows a GC chromatogram of cyclohexanone.
Figure 6:
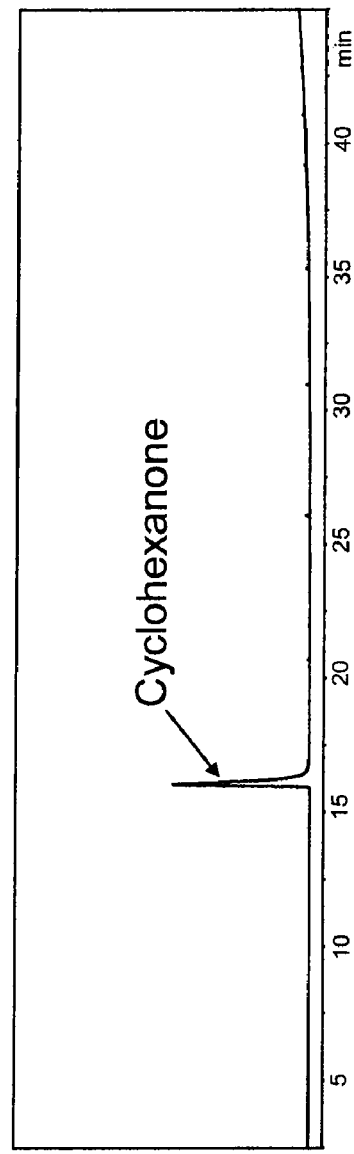

For the purpose of identifying the specified component A, cyclohexanone (Wako Pure Chemical Industries, Ltd., guaranteed reagent) was purchased. Cyclohexanone was placed into a 1.5 mL vial, and subjected to a gas chromatography analysis on cyclohexanone using the solid phase micro extraction method similarly to the case of the urine samples. As a result, the present Applicants ascertained that the retention time of the specified component A (see, FIG. 6a) corresponded to the retention time of cyclohexanone (see, FIG. 6b). From the agreement on the MS spectrum and of the retention time, the specified component A was identified as being cyclohexanone.

(4) Production of Standard Curve of Cyclohexanone

Aqueous cyclohexanone solutions of 1 μM, 10 μM, and 100 μM were prepared. The aqueous cyclohexanone solution of each concentration in a volume of 50 μL was placed into a 1.5 mL vial, which was then sealed airtight using a lid with septum. The vial was set into a heating block, and incubated at 40° C. for 10 min. A Stable Flex DVB/CAR/PDMS fiber (SUPELCO, Inc., 2-layer fiber, film thickness: 50 μm/30 μm) was inserted into the head space for 40 min. After the volatile components were extracted to the fiber, the analysis was carried out using the gas chromatography analysis conditions which were similar to those described above. The analysis was repeated three times for the aqueous cyclohexanone solution of each concentration. A standard curve was produced by plotting the peak areas and the concentrations of the aqueous cyclohexanone solutions.

Figure 7:
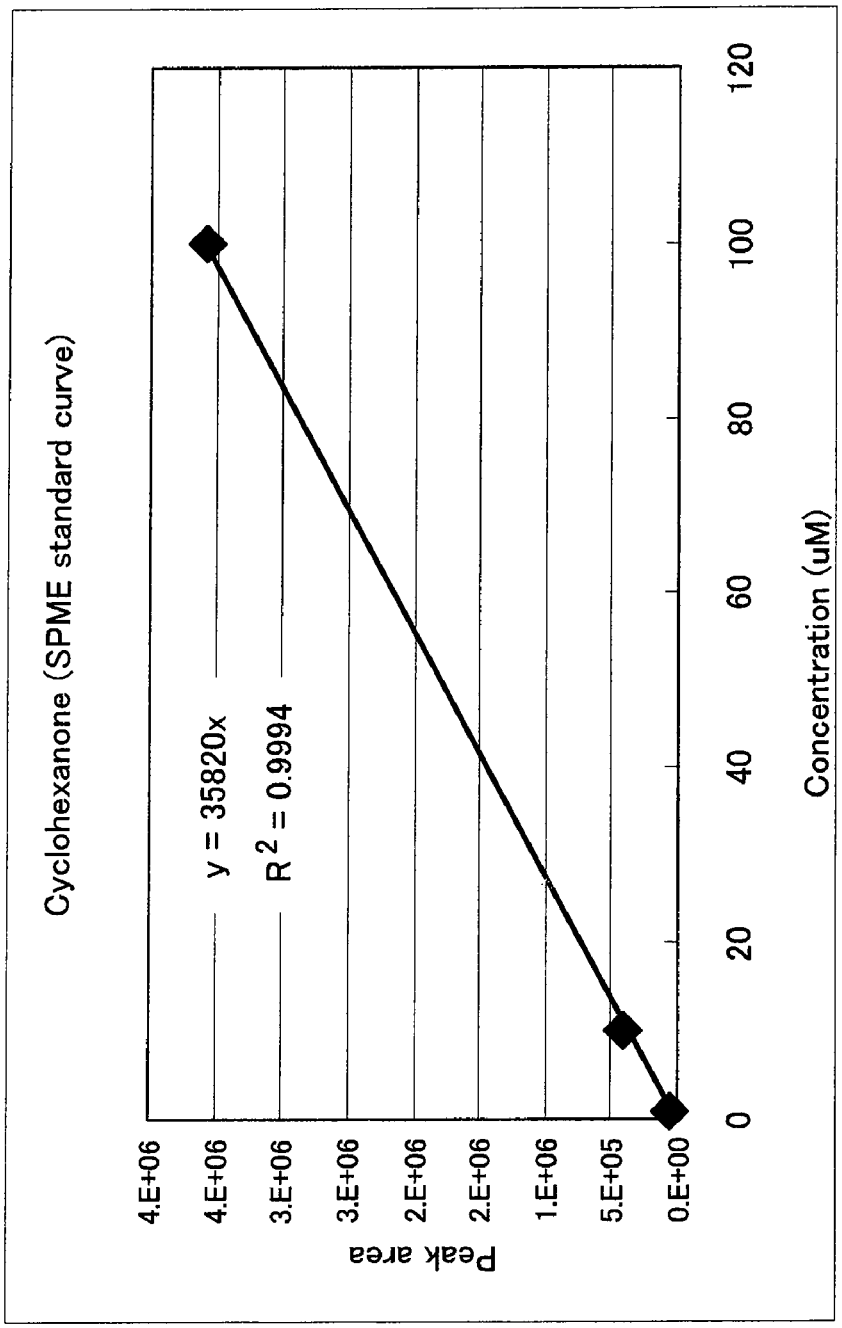
FIG. 7 shows a standard curve of cyclohexanone.

FIG. 7 shows a standard curve of cyclohexanone. The longitudinal axis represents the area of the peak corresponding to cyclohexanone, whereas the horizontal axis represents the concentration (μM) of the aqueous cyclohexanone solution. The coefficient of correlation between the concentration of the aqueous cyclohexanone solution and the peak area was 0.9994, indicating high linearity. As shown in Table 2, the coefficient of variation at a concentration of 1 μM was 20.3%. However, the coefficient of variation at each concentration of 10 μM and 100 μM were 1.6% and 0.8%, respectively.

TABLE 2

Peak Area, Standard Deviation, and Coefficient of Variation of Cyclohexanone

| Cyclo-hexanone | First analysis | Second analysis | Third analysis | Average | Standard deviation | Coefficient of variation (%) |
|---|---|---|---|---|---|---|
| 1 uM | 56541 | 43076 | 65163 | 54927 | 11131.6 | 20.3 |
| 10 uM | 415539 | 427250 | 415539 | 419443 | 6761.3 | 1.6 |
| 100 uM | 3580449 | 3602729 | 3544006 | 3575728 | 29644.8 | 0.8 |

(5) Measurement of Cyclohexanone Concentration in Urine

Using the standard curve shown in FIG. 7, cyclohexanone concentrations in the urine of the human lung cancer patient and the control urine were calculated. As shown in Table 3a, the average cyclohexanone concentration in the urine of the human lung cancer patients was 3.4 μM (from minimum concentration of 1.4 μM to maximum concentration of 7.2 μM). On the other hand, as shown in Table 3b, the average cyclohexanone concentration in the control urine was 0.22 μM (from minimum concentration of 0.2 μM to maximum concentration of 0.4 μM).

TABLE 3a

Cyclohexanone Concentration in Urine of Human Lung Cancer Patients

| Subject No. | Histology | Overall Stage | Cyclohexanone (μM) |
|---|---|---|---|
| 1 | Squamous Cell | 1A | 7.2 |
| 2 | Adenocarcinoma | 1A | 1.4 |
| 3 | NSCLC - NOS | 1A | 3.8 |
| 4 | Squamous Cell | 1A | 3.5 |
| 5 | Adenocarcinoma | 1A | 2.1 |
| 6 | Adenocarcinoma | 1B | 2.5 |
| 7 | Adenosquamous | 1B | 2.3 |
| 8 | Squamous Cell | 1B | 3.2 |
| 9 | Squamous Cell | 2A | 2.0 |
| 10 | Squamous Cell | 2B | 2.6 |
| 11 | Large Cell | 2B | 3.3 |
| 12 | Adenocarcinoma | 3A | 3.4 |
| 13 | Adenocarcinoma | 3A | 5.8 |
| 14 | Adenocarcinoma | 3A | 3.3 |
| 15 | Adenocarcinoma | 3A | 2.0 |
| 16 | NSCLC - NOS | 3B | 5.2 |
| 17 | Adenocarcinoma | 3B | 2.5 |
| 18 | Squamous Cell | 3B | 5.8 |
| 19 | Adenosquamous | 3B | 3.0 |

TABLE 3b

Cyclohexanone Concentration in Control Urine

| Subject No. | Diagnosis | Cyclohexanone (μM) |
|---|---|---|
| 1 | COPD | 0.3 |
| 2 | COPD | 0.4 |
| 3 | COPD | 0.3 |
| 4 | COPD | 0.2 |
| 5 | Asthma | 0.2 |
| 6 | Healthy | 0.2 |
| 7 | Healthy | 0.2 |
| 8 | Healthy | 0.2 |
| 9 | Healthy | 0.2 |
| 10 | Healthy | 0.2 |
| 11 | Healthy | 0.2 |
| 12 | Heart disease | 0.2 |
| 13 | Thyroid disease | 0.2 |
| 14 | Healthy | 0.2 |
| 15 | Asthma | 0.2 |
| 16 | Healthy | 0.2 |
| 17 | Heart disease | 0.2 |
| 18 | Hypertension | 0.2 |
| 19 | Hypertension | 0.2 |

Figure 8:
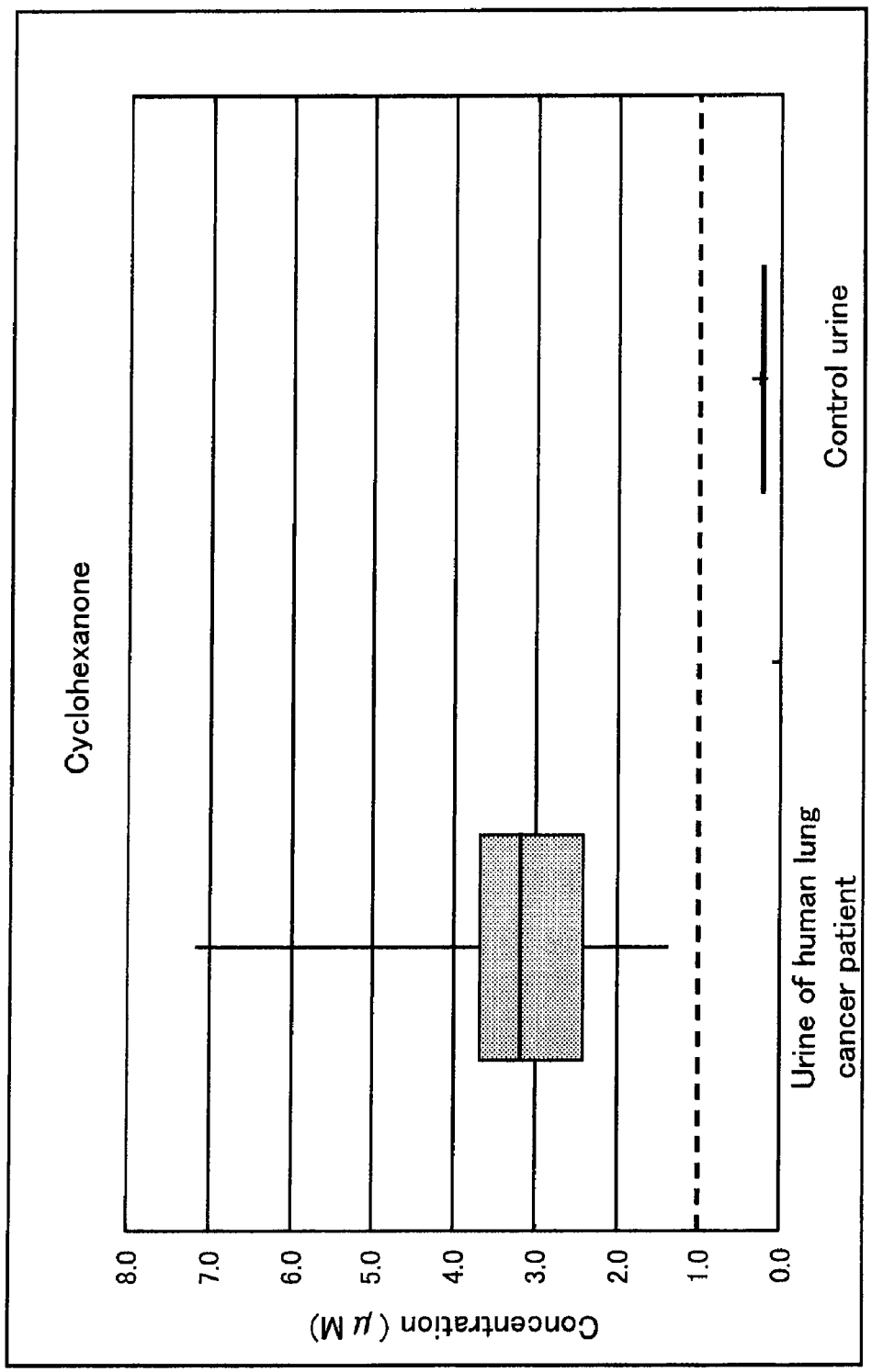
FIG. 8 shows a graph illustrating distribution of cyclohexanone concentration in the urine excreted from the human lung cancer patients and the control urine.

FIG. 8 shows distribution of cyclohexanone concentration in the urine of the human lung cancer patients and control urine. From the aforementioned experimental results, it was identified that the urine excreted from a human contains not less than 1 μM cyclohexanone if he or she is affected with a lung cancer. The dotted line in FIG. 8 indicates 1 μM that is considered to be a threshold as a marker for lung cancer.

Various types of tumor markers have been extensively used in clinical field as markers for diagnosing malignant tumor, determining therapeutic effects, or examining signs of recurrence after surgery. Since almost all conventional tumor markers are proteins or hormones, it has been necessary to collect blood from a subject (mammal), and to measure the concentration in plasma. However, according to the present disclosure, since the tumor marker which is a target of detection is a volatile component contained in urine, an inspection sample can be noninvasively obtained without imposing a burden to the subject.

By comparing volatile components contained in the urine excreted from human lung cancer patients and human non-lung cancer patients, cyclohexanone was specified as one component in the urine that increases when affected with a lung cancer, irrespective of the race and the presence/absence of smoking history. Furthermore, Applicants discovered that a patient is affected with a lung cancer when the cyclohexanone concentration in the urine is not less than 1 µM.

Thus, the cyclohexanone concentration in urine is useful as a marker for lung cancer. According to the present disclosure, efficient determination as to whether or not a patient is affected with a lung cancer is enabled.

What is claimed is:

1. A method for determining whether or not a patient is affected with a lung cancer, the method comprising the steps of:
   obtaining a urine sample from the patient;
   measuring the concentration of cyclohexanone contained in the urine sample; and
   determining that the patient is suffering from lung cancer if the concentration is equal to or greater than 1 µM.

2. The method according to claim 1, wherein the patient is a mammal.

3. The method according to claim 2, wherein the mammal is a primate.

4. The method according to claim 3, wherein the primate is a human.

5. The method according to claim 1, wherein the cyclohexanone concentration is measured using gas chromatography.

6. The method according to claim 1, wherein the lung cancer is selected from the group consisting of squamous cell, adenocarcinoma, non-small cell lung carcinoma (NSCLC), large cell carcinoma and adenosquamous carcinoma.

* * * * *